(12) United States Patent
Mitschke et al.

(10) Patent No.: US 7,519,414 B2
(45) Date of Patent: Apr. 14, 2009

(54) METHOD AND APPARATUS FOR VISUALIZATION OF 2D/3D FUSED IMAGE DATA FOR CATHETER ANGIOGRAPHY

(75) Inventors: Matthias Mitschke, Nürnberg (DE); Norbert Rahn, Forchheim (DE); Dieter Ritter, Fürth (DE); Michael Scheuering, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 843 days.

(21) Appl. No.: 10/860,707

(22) Filed: Jun. 3, 2004

(65) Prior Publication Data

US 2005/0015006 A1    Jan. 20, 2005

(30) Foreign Application Priority Data

Jun. 3, 2003   (DE) ................ 103 25 003

(51) Int. Cl.
*A61B 5/00*    (2006.01)
(52) U.S. Cl. .............. 600/424; 382/128; 382/130; 382/131; 378/62; 378/63
(58) Field of Classification Search ............ 600/407, 600/431, 433, 435, 424, 427, 436; 382/128, 382/130; 378/62, 63
See application file for complete search history.

(56) References Cited

U.S. PATENT DOCUMENTS

| | | | |
|---|---|---|---|
| 5,914,725 A * | 6/1999 | MacInnis et al. ............ 345/441 |
| 6,317,621 B1 * | 11/2001 | Graumann et al. .......... 600/424 |
| 6,370,417 B1 * | 4/2002 | Horbaschek et al. ........ 600/424 |
| 6,711,433 B1 * | 3/2004 | Geiger et al. ............... 600/431 |
| 2003/0014034 A1 * | 1/2003 | Strobel ....................... 604/407 |
| 2003/0043969 A1 * | 3/2003 | Menhardt ................... 378/210 |

OTHER PUBLICATIONS

Fahrig et al.'s "Use of C-arm System to Generate True Three-dimendional Computed Rotational Angiograms: Preliminary In Vitro and In Vivo Results," American Society of Neuroradiology, Sep. 18, 1997, vol. 18, pp. 1507-1514.*

* cited by examiner

*Primary Examiner*—Long V Le
*Assistant Examiner*—Vani Gupta
(74) *Attorney, Agent, or Firm*—Schiff Hardin LLP

(57) ABSTRACT

In an image post-processing method and apparatus for 3D visualization of 2D/3D fused image data for use in catheter angiography in an endovascular interventional procedure, upon forward movement of a micro-catheter through blood vessel in the interventional procedure, x-ray images are acquired from different projection directions and are subjected to a pattern recognition algorithm for edge-based segmentation of the image regions filled by the micro-catheter, with all remaining image regions being masked out. The segmented projection exposures are prepared by a 3D reconstruction algorithm to obtain an image data set for (pseudo-) three-dimensional representation of the micro-catheter. This image data set are intraoperatively registered and fused with an image data set acquired from an angiographic pre-examination for three-dimensional visualization of the vessel topography. The reconstructed 3D representation of the catheter is mixed into the three-dimensionally prepared representation of endovascular blood vessel sections to be treated.

8 Claims, 3 Drawing Sheets

METHOD AND APPARATUS FOR VISUALIZATION OF 2D/3D FUSED IMAGE DATA FOR CATHETER ANGIOGRAPHY

BACKGROUND OF THE INVENTION

1. Field of the Invention

The present invention concerns a 3D image post-processing method of the type wherein an x-ray contrast agent is administered via a micro-catheter (catheter angiography), as well as a medical-technical apparatus for three-dimensional representation of sections of the blood vessel system of a patient that, in particular in the field of coronary angiography, can be used to diagnose diseases of the coronary vessels, as well as in the field of neuro-angiography for (pseudo-) three-dimensional vascular imaging in the framework of an endovascular intervention.

2. Description of the Prior Art

For preventative treatment of coronary and cerebral aneurysms, angiomas and other arterial-venous malformations (AVM), endovascular interventions are ever more frequently employed today as an alternative to coronary or neurosurgical procedures. In the preliminary stages of an endovascular intervention, a contrast agent-intensified angiographic examination of the blood vessel sections affected by a vessel anomaly is normally implemented.

In catheter angiography, the blood vessels to be examined are made visible by x-ray exposures after injection of a contrast agent. For example, a micro-catheter of approximately 1.5 mm external diameter, inserted intravascularly via the inguinal artery, is moved to the blood vessels to be examined. Since this is a minimally-invasive method, catheter angiography is today used only seldomly for purely diagnostic purposes. For example, using modem micro-catheters (which typically have an external diameter of approximately 0.6 mm), in stroke patients the location of a vessel narrowing (stenosis) caused by arteriosclerosis or a blood clot can be found inside the skull and, for example, thromboses can be loosened in an endovascular interventional procedure with the aid of a fibrinolytic medicine.

The intravascular insertion of a micro-catheter for endovascular therapy of a blood vessel deformation, as well as the navigation of this catheter within the blood vessel system to be treated, is a difficult and demanding procedure, since the catheter must be guided through a number of vessel branchings. This procedure can be significantly simplified by a 3D visualization of the sections of the vessel system to be examined. Conventionally, the navigation of the catheter through the vessel tree is monitored fluoroscopically. In order to show the blood vessels, contrast agent is thereby applied by the tip of an intravascularly inserted micro-catheter in order to make the blood vessels in the environment of the catheter tip visible in the x-ray image. In order to reconstruct the three-dimensional structure of the vessel tree, a number of x-ray images are necessary from various directions. Afterwards the catheter is moved further forward without the imaging method being continued during this movement.

Systems for angio-cardiography are specially designed for the display of heart chambers, heart valves and heart vessels. They must satisfy all requirements for the diagnosis and must support the implementation of the appropriate therapeutic procedures that are possible with the procedures of interventional cardiology. Among these procedures are, for example, vessel dilation as well as the expansion of the heart valve cross-section using balloon catheters, thrombolysis with pharmaceuticals applied via catheter directly at the location of a lesion, and the opening of blocked coronary arteries by laser beams.

Since the risk for the patient increases with the duration of the examination or procedure, for the patient's interest, as well as for economic reasons, an invasive examination of the heart should be implemented in a manner that saves as much time as possible. The same is true for therapeutic procedures within interventional cardiology. An imaging system for this purpose should optimally allow simultaneous imaging in two different projection directions (biplanar operation), or should allow a rapid change (switching) between two projection directions. In the exposure, a biplanar system significantly eases the orientation during the positioning of the catheter and reduces the need of contrast agent in the exposures and the retention period of the catheter in the vessel, since two projection directions can be acquired at the same time with a single injection. At the same time, a quantitative description or classification of existing stenoses is simplified by the simultaneous biplanar representation.

The coronary vessels are spread over the curved heart surface, and therefore can be represented only from a single projection direction without distortions in sections. For this reason, and for the elimination of overlappings of individual vessels, a number of different projections are necessary for a complete examination of the coronary system.

Digital subtraction angiography (DSA), computed tomography angiography (CTA), magnetic resonance or nuclear magnetic resonance angiography (MRA) and ultrasound diagnosis methods (for example Doppler sonography and color-coded duplex sonography) (CCDS) are available today for the diagnosis of blood vessel diseases. Primarily, developments in the field of computed tomography (CT), magnetic resonance tomography (MRT) and ultrasound diagnostics have clearly limited the need for invasive examination methods (for example, DSA) in the framework of the vessel diagnosis. It can be expected of the newest developments, in particular in the field of MR angiography and ultrasound diagnostics, that in the near future the primary vessel diagnostics will be implemented almost completely with non-invasive, more patient-friendly examination methods.

In the following, a brief description is provided for the most important examination methods used in the framework of a preoperative endovascular intervention, knowledge of which is necessary for the comprehension of the present invention (DSA, CTA, MRA and computer-aided 3D rotation angiography).

Digital subtraction angiography (DSA) is an invasive examination method that today is accepted ever more as the radiological standard method for diagnosis of vessel diseases—in spite of large advances in the field of CT and MR angiography. It requires an arterial puncture and the insertion of a catheter into the concerned examination region, the administration of an x-ray contrast agent (normally containing iodine), and a relatively high radiation exposure. An advantage is the (in comparison to other imaging methods) comparably high spatial and temporal resolution. Only the perfused lumen of a vessel, however, can be shown with DSA. Moreover, with this examination method vessel narrowings (stenoses) caused by atherosclerotic deposits (plaque formation) on the inner walls cannot be verified, or can be verified only indirectly. The use of invasive DSA consequently is used only when an interventional measure (such as, for example, a balloon dilation or stent introduction) is additionally planned, for the vessel representation.

In DSA, two x-ray exposures are produced at a temporal interval from one and at the same viewing angle: an exposure of the blood vessels not yet filled with contrast agent (what is known as the mask image) and an exposure of the vessel filled with an x-ray contrast agent after the contrast agent injection (the fill image). The x-ray images are then subtracted from one another, so congruent image portions of bones and soft parts are eliminated such that only the blood vessels filled with the x-ray contrast agent are shown. Typically, before the subtraction a logarithmization of the intensity signals corresponding to the fill and mask images is done, such that the obtained difference image is directly proportional to the contrast agent concentration and all tissue structures outside of the blood vessels to be examined are eliminated by the subtraction.

Computed tomographic angiography (CTA) is a minimally-invasive examination method with a high spatial resolution but a comparably limited temporal resolution, for which, by spiral computed tomography, a (pseudo-) three-dimensional representation of the larger blood vessels is generated. Similar to DSA, the method requires the administration of contrast agent (normally containing iodine) and a non-negligible radiation exposure. A significant diagnostic advantage of CTA, however, is that it allows detection of atherosclerotic plaque, as well as the possibility to assess the wall structure of larger vessels, and the exact determination of the lumen width of a vessel. In comparison to DSA, the CTA offers a better diagnostic conclusion in the preliminary stage of percutaneous endovascular interventions. Conventional reconstruction methods enable a 3D representation of larger vessels, but require a relatively long post-processing time for 3D reconstruction from x-ray images acquired from various projection directions.

Magnetic resonance imaging or magnetic resonance angiography (MRA) is a non-invasive examination method with very good spatial and temporal resolution and a relatively high contrast resolution. Improvements in the diagnostic significance, above all in the area of smaller vessels, can be achieved by the increasing use of paramagnetic contrast agents. Similar to computer tomography, magnetic resonance tomography allows both the perfused lumen and changes of the vessel walls to be shown. Due to the higher contrast resolution, however, it is clearly superior to computed tomography. Image post processing and 3D reconstruction of large vessel sections are possible in an extremely short time.

In order to improve the topographic representation of the vessel tree, optical realization of the third dimension in angiographic studies has been studied since the 1970s. Rotation x-ray examinations of the brain where first introduced in clinical practice, wherein all auxiliary projections were achieved by rotation of an x-ray tube around the head of a patient, and thus stereoscopic views of the cerebral blood vessels were possible. The introduction of computer-aided rotation angiography brought the technical breakthrough to reconstruct the (pseudo-) three-dimensional representations with isotropic resolution from the raw projection data, as is described in the article "Use of a C-Arm System to Generate True Three-Dimensional Computed Rotational Angiograms: Preliminary In-Vitro and In-Vivo Results" (AJNR 1997, Vol. 18, pp. 1507 through 1514) by R. Fahrig, among others, 3D rotation angiography has proven to be a valuable complement to conventional angiographic examination methods, both in diagnostic and therapeutic procedures. From the spatial information that is acquired at a workstation in the interactive evaluation of 3D reconstructions of x-ray images acquired from a number of projection directions, 3D rotation angiography is far superior to a conventional digital biplanar subtraction angiography in the assessment of neck aneurysms and the relation to adjacent blood vessels. The 3D reconstructions of the vessel structure are graphically visualized using a volume rendering technique (VRT), multiplanar reformatting (MPR) or maximal intensity projections (MIP). Moreover, they can be rotated and thus considered from various perspectives. Due to the high speed of the post-processing software, 3D angiography has today developed into a tool that can be directly used in the planning and implementation of endovascular interventions.

In the last few years, further improvements have been made to the imaging systems and the software to generate 3D images. Meanwhile, 3D imaging systems are available on the market from various angiography apparatus manufacturers. Given patients on whom DSA examinations have been implemented with faster image reconstruction and high image quality, 3D angiography has proven to be more advantageous than the standard DSA in the evaluation and treatment planning of intracranial aneurysms. In contrast to rotation angiography, an image can be viewed from an arbitrary perspective. With regard to arterial stenoses, the three-dimensional image can expose anomalies or the degree of a lesion that cannot be determined in planar views. Any arbitrary perspective is possible, including viewing angles that would be impossible with DSA due to the limited mobility of the angiographic apparatuses.

SUMMARY OF THE INVENTION

An object of the present invention is to provide an image acquisition and processing technique, with which a 3D representation of blood vessels is enabled in the context of a contrast agent-free endovascular intervention, for better orientation in the navigation of an intravascularly inserted micro-catheter.

The present invention concerns a computer-aided 3D image post-processing method as well as a medical-technical apparatus for three-dimensional representation of sections of the blood vessel system of a patient. The inventive method is particularly suitable for use in the field of coronary and neuro-anglography for (pseudo-) three-dimensional cardio- or cerebro-vascular imaging for the purpose of supporting the treating specialist doctor in the implementation of an endovascular intervention, in which an intravascularly inserted micro-catheter is navigated to the blood vessel sections to undergo therapy.

The inventive method uses a 3D visualization of 2D/3D registered data sets. Instead of a conventional two-dimensional representation of the fusion result of the images (acquired from DSA, MRA, CTA and/or 3D rotation angiography) of the vessel system of the patient to be examined, with the x-ray images acquired during an endovascular intervention (intraoperatively) from different projection directions, in the inventive method a (pseudo-) three-dimensional representation (reconstructed from a number of x-ray images) of the micro-catheter intravascularly inserted during a percutaneous endovascular intervention is mixed ("back-projected") into the 3D representation of the vessel system acquired from an angiographic pre-examination. Using known 3D visualization techniques such as, for example, the 3D volume rendering method (VRT), in this manner slice planes of the back-projected catheter can be emphasized with the blood vessels. The diagnosing physician now has the possibility to consider the operating field from different perspectives based on the three-dimensionally prepared data, which leads to a simplified orientation in the vessel tree in an endovascular intervention. The temporal decoupling of the angiographic pre-examination and endovascular intervention has the advantage that no application of contrast agent via the catheter tip is necessary during the therapeutic procedure. This represents a significant improvement in patient comfort.

DESCRIPTION OF THE PREFERRED EMBODIMENTS

Figure 1:
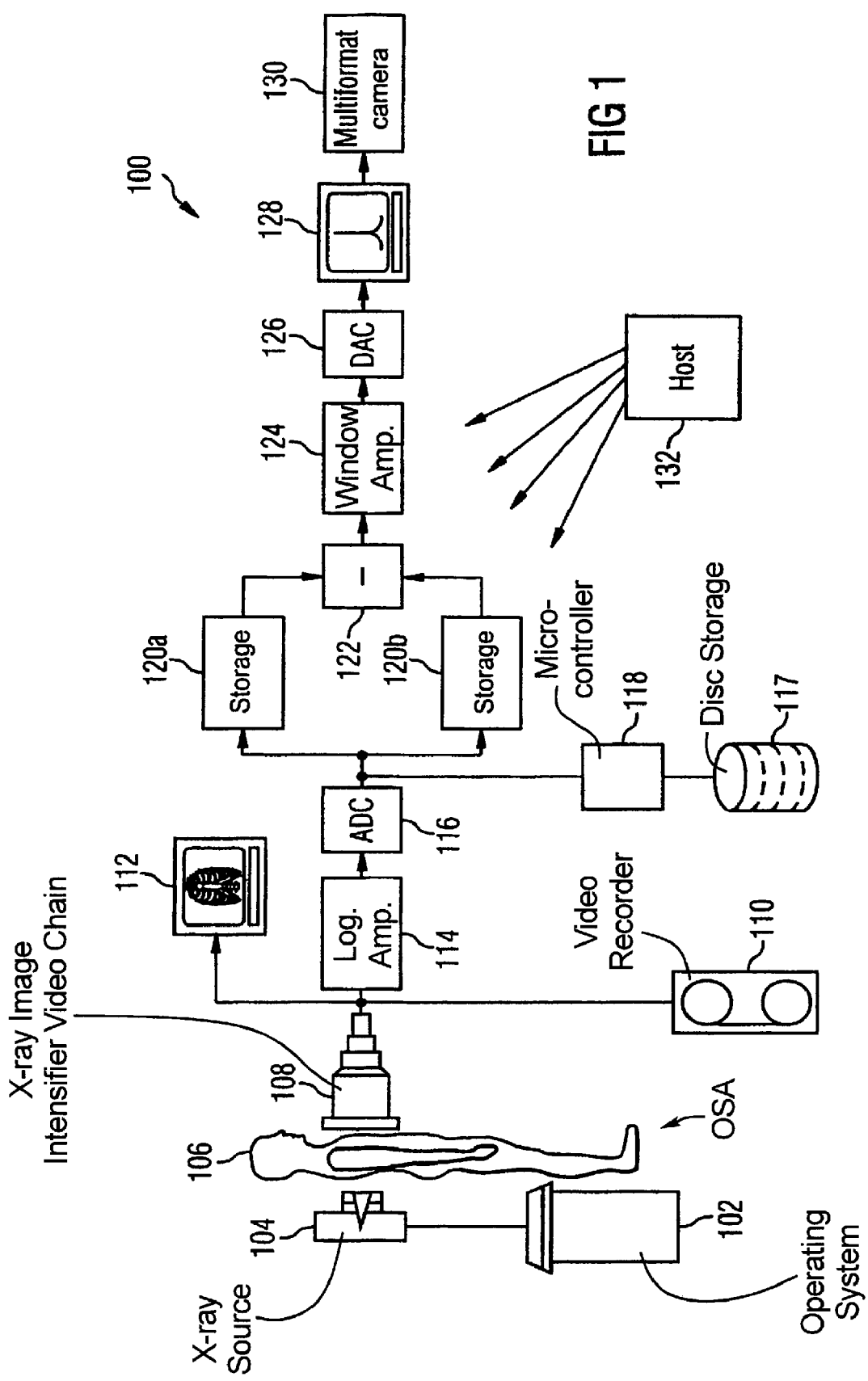
FIG. 1 is a schematic block diagram of a medical-technical apparatus (a DSA system, as an example) for angiographic representation of parts of the blood vessel system of a patient from at least two different projection directions constructed and operating according to the invention.
Figure 3:
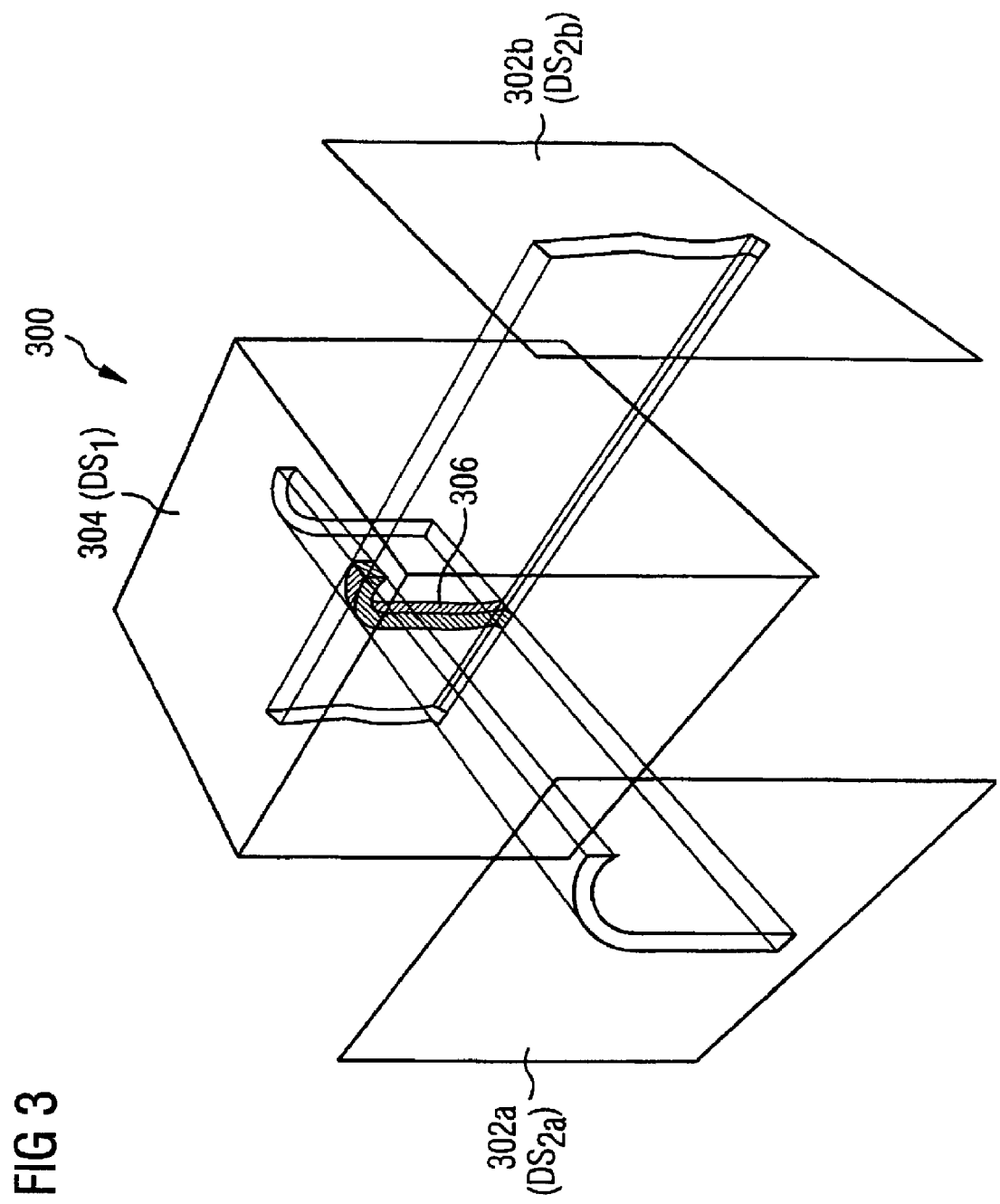
FIG. 3 illustrates the mixing of a 3D reconstruction of the micro-catheter used in an endovascular intervention into the three-dimensionally prepared representation of the x-ray exposures (acquired in an angiographic pre-examination) of the blood vessels to be treated in accordance with the invention.

In the following, the invention imaging method as illustrated in FIG. 3 is first described in detail. The functioning of the system components depicted in FIG. 1 is subsequently explained.

As an exemplary embodiment of the invention, a computer-aided imaging and image post-processing method is described for angiographic representation of aneurysms, angiomas and other arterio-venal malformations (AVM) of parts of the blood vessel system of a patient. A micro-catheter 306 (which can be inserted intravascularly) serves for the injection of an x-ray contrast agent. Before the beginning of an endovascular intervention, a contrast agent-intensified angiography pre-examination (S1) for two-dimensional representation of the parts of the blood vessel system to be treated is implemented from at least two different projection directions, and a 3D reconstruction method (S2) is applied for the purpose of acquisition of a first image data set (DS1) in order to obtain a three-dimensional representation of the vessel topography.

During a temporally subsequent (and thus separate) implementation of an endovascular intervention, x-ray images 302a and 302b are then acquired from at least two different projection directions upon continuous forward movement of the micro-catheter 306 through a blood vessel to be treated. The x-ray images 302a and 302b are subjected to a pattern recognition algorithm for edge-based segmentation (S4) of the image regions filled by the micro-catheter 306, with all remaining image regions are masked out (S5).

The segmented projection exposures are then further processed by a 3D reconstruction algorithm (S6), for example a 3D volume rendering method (VRT) in order to obtain a second image data set (DS2) for (pseudo-) three-dimensional representation of the micro-catheter 306.

A semi-transparent 3D representation of the micro-catheter 306 is calculated in accordance with the invention by determining suitable opacity values for the grey value representation of the surfaces of the three-dimensionally reconstructed micro-catheter 306. Alpha blending techniques are used to generate the transparency effects.

The obtained image data sets (DS1, DS2) then can be intraoperatively registered and fused, with the reconstructed 3D representation of the micro-catheter 306 being mixed into the three-dimensionally prepared angiographic representation of the endovascular blood vessel sections 304 to be treated.

A diagram to illustrate the inventive method is shown in FIG. 3. The 3D reconstruction 300 can be interactively post-processed on a workstation 132 and be considered from arbitrary viewing angles.

The x-ray contrast images inventively acquired from the angiographic pre-examination and from different projection directions also can be used as a basis for calculation of endoluminal perspectives, and thus for virtual angioscopy.

According to a further embodiment of the invention, the Cartesian spatial coordinates of the micro-catheter 306 are calculated in each three-dimensional reconstruction of x-ray exposures 302a and 302b of the second image data set (DS2), and these coordinates are mixed into the angiographic representation 300 that is three-dimensionally visualized on a display device 128, and as needed coordinates are achieved. The path of the micro-catheter 306 through the blood vessel system is detected upon the implementation of the endovascular intervention and mixed into the angiographic representation 300 three-dimensionally visualized at the display device 128.

A computer software program product is also inventively provided which implements the computer-aided 3D imaging and image post-processing method described above when it is loaded into and executed by a computer 132 with the display device 128.

A medical-technical apparatus 100 for three-dimensional angiographic representation of the blood vessels of a patient 106 acquired in the framework of digital subtraction angiography (DSA), suitable for implementing the inventive method, is shown in FIG. 1. This apparatus 100 can be particularly advantageously used in the context of a preoperative diagnosis of arteriosclerosis, aneurysms, angiomas and other anterior-venal malformations (AVM), for example in the area of the cerebral blood vessels, as a pre-examination for a percutaneous endovascular intervention with the aid of an intravascularly insertable micro-catheter. The apparatus 100 has an intravascularly insertable micro-catheter 306 to inject an x-ray contrast agent into the blood vessels and a digital DSA system (as schematically Indicated by the example of the DSA system having an x-ray source 104 operated by an operating system 102, and an x-ray intensifier video chain 108)to acquire steps (S1, S3) x-ray contrast images 302a and 302b from at least two different projection directions.

A suitable 3D angiography system to implement CTA, MRA or 3D rotation angiography alternatively can be used for three-dimensional representation of the blood vessels to be examined.

A computer 132 serves to implement pattern recognition, image post-processing and 3D reconstruction algorithms steps (S2, S4, S5, S6, S7) for the purpose of acquisition, registration and fusion of image data sets (DS1, DS2) for three-dimensional visualization of the vessel topographic and the intravascularly inserted micro-catheter 306. The registered and fused image data 300 can be graphically shown at the display device 128.

The image signals acquired via the x-ray image intensifier video chain 108 of the DSA system are supplied to a logarithmic amplifier 114 and an analog-to-digital converter 116. A first memory 120a is provided for buffering the fill image 202b (an x-ray contrast exposure of the blood vessels filled with a contrast agent) acquired by digital subtraction angiography (DSA), and a second memory 120b is provided to buffer the empty exposure of the mask image 202a acquired in DSA (an x-ray contrast exposure of the blood vessels not filled with contrast agent).

Figure 2:
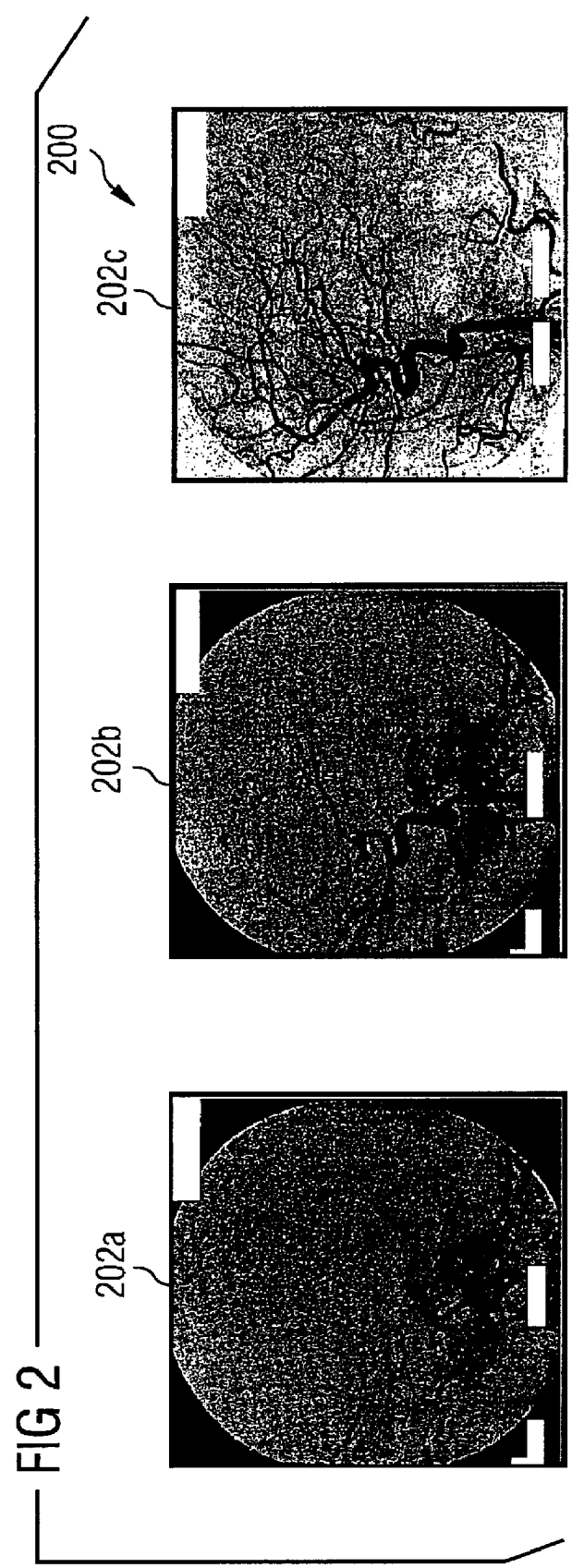
FIG. 2 shows the mask image, fill image and the subtraction image of the grey value representations obtained in a DSA of parts of the blood vessel system to be examined.

The mask image 202a, the fill image 202b and the subtraction image 202c, as grey scale value representations (obtained in digital subtraction angiography (DSA)) of parts of the blood vessel system of a patient, are shown in FIG. 2.

The memory contents are subtracted in a further computer 122, pass through a computer 124 for window amplification, and are finally converted in a digital-to-analog converter 126 back into analog video signals that can be shown on the monitor 128. In addition to the actual mask image and fill image, all images of a scene are stored in a raw data memory. This can be a video recorder 110 with high signal-to-noise ratio, a digital disc storage 117 (a Winchester disk) operated by a microcontroller 118, or a large semiconductor memory with a storage capacity of more than 20 Mbyte. The displayed image can be captured by a multi-formed camera 130. A host computer 132 provides the desired execution, controls the computers 122 and 124 provided for the processing of the image data, and administers the images of the raw data storage 110 and 117.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for visualizing 2D/3D fused image data for catheter angiography, comprising the steps of:
   obtaining contrast agent-intensified angiographic 2D data of blood vessels of a patient from at least two different projection directions;
   generating a 3D visualization of a vessel topography of said blood vessels from said angiographic 2D data;
   acquiring a plurality of x-ray images of the subject respectively from at least two different projection directions with a micro-catheter inserted in the subject;
   generating a 3D reconstruction from said x-ray images for three-dimensional visualization of the micro-catheter; and
   mixing the 3D visualization of the micro-catheter into the 3D visualization of the vessel topography.

2. A method as claimed in claim 1 executing a pattern recognition for edge-based segmentation of image regions filled by said micro-catheter and masking out all remaining image regions.

3. A method as claimed in claim 1 comprising calculating a semitransparent 3D representation of said micro-catheter.

4. A method as claimed in claim 3 comprising employing an alpha blending technique for generating said semitransparent representation.

5. A method as claimed in claim 1 comprising calculating Cartesian spatial coordinates of said micro-catheter in each 3D reconstruction of said x-ray images, and blending said coordinates into the three-dimensional visualization of the vessel topography.

6. A method as claimed in claim 1 comprising detecting a path of movement of said micro-catheter through said blood vessels during an endovascular interventional procedure, and mixing said path into said 3D visualization of the vessel topography.

7. A method as claimed in claim 1 comprising generating 3D contrast images and using said 3D contrast images for calculating endoluminal perspectives in different portions of said blood vessels for virtual angioscopy.

8. An apparatus for angiographic representation of blood vessels comprising:
   a micro-catheter adapted for insertion in a subject for injecting an x-ray contrast agent into blood vessels in the subject;
   a digital angiography system adapted for interaction with the patient for acquiring x-ray contrast images of the blood vessels from different projection directions, said digital angiography system obtaining contrast agent-intensified angiographic 2D data of said blood vessels from at least two different projection directions and acquiring x-ray images from at least two different projection directions with the micro-catheter inserted in the patient;
   a computer for constructing a 3D visualization of a vessel topography of said blood vessels from said angiographic 2D data and for generating a 3D reconstruction of the micro-catheter from said x-ray images, and for mixing the 3D reconstruction of the micro-catheter into the 3D visualization of the vessel topography in a fused image; and
   a display for displaying said fused image.

* * * * *